United States Patent [19]

Cliff et al.

[11] 4,212,840
[45] Jul. 15, 1980

[54] EXTRUSION APPARATUS AND METHOD FOR EXTRUDING ABRASIVE PASTES

[75] Inventors: George S. Cliff; Jack Willocks, both of Macclesfield, England

[73] Assignee: Imperical Chemical Industries Limited, London, England

[21] Appl. No.: 940,872

[22] Filed: Sep. 8, 1978

[30] Foreign Application Priority Data

Sep. 19, 1977 [GB] United Kingdom ............... 38878/77

[51] Int. Cl.² ............................................. B28B 7/36
[52] U.S. Cl. ................................... 264/338; 249/112;
264/176 R; 425/89; 425/376 R; 425/376 A
[58] Field of Search ................ 264/338, 176; 425/376, 425/89; 249/112

[56] References Cited

U.S. PATENT DOCUMENTS

| | | | |
|---|---|---|---|
| 3,380,121 | 4/1968 | Chittenden et al. | 249/112 |
| 3,442,481 | 5/1969 | Di Stasio | 425/89 |
| 3,479,704 | 11/1969 | Reed | 425/89 |
| 4,003,545 | 1/1977 | Tanaka | 249/112 |

FOREIGN PATENT DOCUMENTS

| | | | |
|---|---|---|---|
| 229367 | 2/1925 | United Kingdom | 264/176 |
| 541868 | 12/1941 | United Kingdom | 264/176 |
| 583525 | 12/1946 | United Kingdom | 264/176 |
| 1371662 | 10/1974 | United Kingdom | 264/176 |

*Primary Examiner*—Donald J. Arnold
*Attorney, Agent, or Firm*—Cushman, Darby & Cushman

[57] ABSTRACT

This invention concerns an improved apparatus for extruding abrasive pastes, especially those which contain ground glass together with polymerizable material, and which comprises a conventional piston and cylinder extrusion apparatus in which the working surfaces are protected by a replaceable lining system consisting of a thin tubular liner and two discs substantially closing its ends and enclosing the paste to be extruded. In the preferred embodiment (FIG. 1) the lining system is made of polypropylene.

5 Claims, 4 Drawing Figures

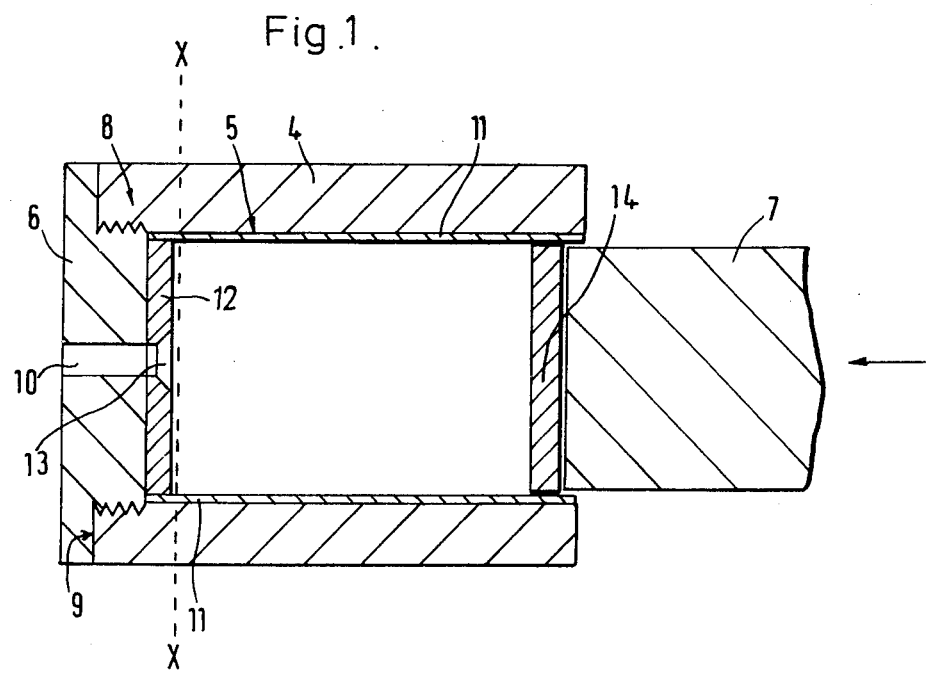
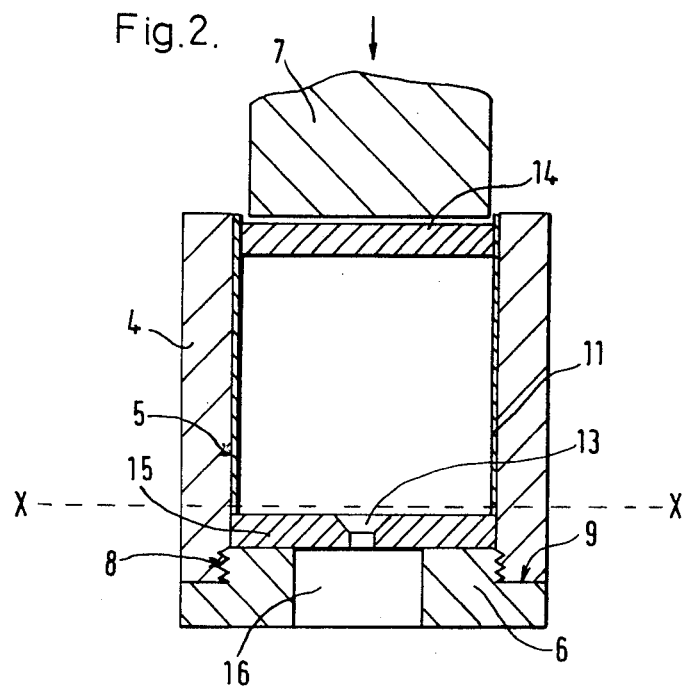

EXTRUSION APPARATUS AND METHOD FOR EXTRUDING ABRASIVE PASTES

This invention relates to improved extrusion apparatus for use with abrasive paste-like materials, and especially such materials comprising at least 50% by weight of ground glass together with a polymerisable material, for example dental filling compositions.

Extrusion apparatus of the general type having a cylindrical piston for compressing paste-like material within a bore, generally complementary to the piston, and leading at its inner end to an external orifice, are well known. Such apparatus are widely employed in situations where it is necessary to charge small quantities of paste-like material from a bulk supply into individual containers for sale and ultimate use. Normally such apparatus are constructed with the piston and bore of metal, or other material which can be machined to accurate tolerances, so that the piston is a good fit inside the bore and leakage of material past the piston is thereby minimised during the extrusion process. These apparatus are consequently relatively expensive and are not suited for use with abrasive paste-like materials, since considerable wear quickly takes place on those surfaces of the piston and bore exposed to the material. As a result, considerable leakage of material past the piston occurrs, the extrusion process becomes inefficient, and complete replacement of the piston and bore is often necessary with the attendant expense and inconvenience.

One partial solution to the problem of excessive wear is provided by using solvents or diluents to lubricate the working surfaces of the apparatus especially when the abrasive pastes are viscous. However, this procedure is not suitable for all abrasive pastes, for example dental filling compositions, and only reduces rather than eliminates the wear.

We have now discovered, and herein lies our invention, that such apparatus can be adapted for use with abrasive paste-like materials by using a simple, cheap, lining system in the cylinder bore, which can be readily replaced and which minimises the wear to the cylinder and piston by preventing significant contact of the abrasive material therewith.

According to the invention we provide an extrusion apparatus of the general type which includes a cylindrical piston for compressing paste-like material within a bore, generally complementary to the piston, and leading at its inner end to an external orifice; wherein in addition the bore is provided with a replaceable lining system of plastics material, this system comprising a tubular liner, closely fitting against and substantially covering the side-wall of the bore, said liner being substantially closed at its end nearest the orifice, by a first replaceable disc defining a central hole of diameter not larger than that of the orifice, and at its other end, by a second replaceable disc which is capable of slidable movement within the space enclosed by said liner under the influence of said piston.

The liner may be formed from a thin continuous tube, but is preferably formed from a thin sheet of plastics material, for example as stated above, of such dimensions and resilience that it can assume an essentially tubular form without overlap, when inserted into the bore of the apparatus. The maximum thickness of the wall of the liner is such that in operation the piston can still move freely within the space enclosed by the liner, but is conveniently in the range, for example, 0.5–3.0 mm., and preferably of the order of 1.0 mm.

The first and second replaceable discs may preferably be of the same diameter such that they are both a close but slidable fit within the space enclosed by the liner. However, conveniently, when the apparatus is to be used with viscous abrasive pastes, the second replaceable disc may be a looser fit within the liner than the first disc. This reduces the drag between the second disc and the wall of the liner, and generally results in insignificant losses of paste.

Particulary suitable plastics materials are, for example, polypropylene, polytetrafluoroethylene, high density polyethylene or nylon, of which polypropylene is especially preferred when the apparatus is used for extrusion of dental filling compositions.

In order that the invention may be more fully understood, several specific embodiments of an extrusion apparatus according to the invention will now be described, by way of example only and with reference to the accompanying drawings, in which:

FIG. 1 is a sectional side-elevation of a first embodiment;

FIG. 2 is a sectional side-elevation of a second embodiment;

Figure 3:
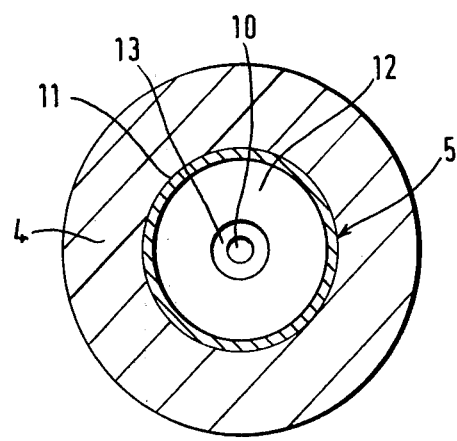
FIG. 3 is a cross-sectional view about the line X—X in FIG. 1 or 2 in the direction of the arrow.

The particular embodiment shown in FIG. 1 comprises a tubular body 4 defining a cylindrical bore 5 open at one end and closed at the other by an end-cap 6, and a cylindrical piston 7 of similar diameter to the bore 5 and which is coupled to an operating means (not shown) for driving the piston 7 progressively into the bore 5 through its open end in the direction arrowed. The end cap 6 is threaded about its periphery and is thereby screwably engaged with a complementary threaded portion 8 in the end of the bore 5. The end-cap 6 is also provided with a flange 9, which abuts the end of the body 4 when the end-cap is screwed into the threaded portion 8 of the bore 5, and a central passage 10, of circular section, which passes through the end-cap and forms the external orifice of the apparatus.

A thin, replaceable, tubular liner 11 is situated against the side-wall of the bore 5. This liner 11 is formed by constraining a thin, resilient rectangular sheet of suitable plastics material, for example polypropylene, by its opposite edges, the sheet being of such dimensions that when it is inside the bore 5, it abuts the end-cap 6 and forms a tube closely fitting against and substantially covering the side-wall of the bore 5, but without any mutual overlapping of the opposite edges of the sheet. The liner 11 is sufficiently thin so that the piston 7 can move freely within the space defined thereby, and the resilience of the sheet ensures that the liner remains a close fit within the bore 5.

The liner 11 is substantially closed at the end abutting the end-cap 6 by a first replaceable disc 12, which is of similar diameter to the internal diameter of the liner so that it is a slidable fit therein. The disc 12 is provided with a central funnel-shaped duct 13 passing through it. This duct 13 has the same diameter as the passage 10 in the end-cap 6 for part of its length, but tapers to a larger diameter on the side of the disc away from the end-cap 6. The liner 11 is substantially closed at its other end by a second replaceable disc 14 which is similar to the first disc 12, but does not have a duct.

The replaceable discs 12 and 14 are conveniently of the same material as the liner 11, for example polypropylene, but are substantially thicker than the liner 11, for example of thickness in the range 4.0–30.0 mm.

The liner 11 and replaceable discs, 12 and 14, together form the replaceable lining system.

The particular embodiment shown in FIG. 2 is generally similar to that depicted in FIG. 1, but differs in respect of the construction of the end-cap and first replaceable disc. Thus, the first replaceable disc 15 is of essentially the same diameter as the bore 5, so that the liner 11 abuts the first replaceable disc 15 rather than the end cap 6. Also the end cap 6 has a central passage 16 similar to that (10) in the first embodiment, but which is substantially larger in diameter than the narrowest part of the funnel-shaped duct 13 in the first replaceable disc 15.

When operating the first embodiment, the end-cap 6 is first screwed into place in the bore 5 and the rectangular sheet constituting the liner 11 is fitted into the bore 5 until it abuts the end-cap 6. The first replaceable disc 12 is then slid inside the liner 11 to contact the end-cap 6 so that the narrowest part of the funnel shaped duct 13 adjoins the passage 10. The abrasive paste-like material to be extruded is then charged into the space defined by the inner wall of the liner 11 which space is then closed by the second replaceable disc 14. The piston 7 is then moved (in the direction arrowed) against the disc 14 under the influence of the operating means, which may be any known suitable mechanism for imparting progressive movement to the piston 7, for example a hand operated wheel geared to a screw threaded rod attached to the rear of the piston 7.

The abrasive paste-like material is thus progessively compressed by the disc 14 so that it is extruded through duct 13 and passage 10 out of the apparatus, whereafter it may be cut off by any known suitable cutting means, for example by a thin wire, knife-edge or scissors arrangement moving across the hole 10, when the required length of paste-like material has been extruded.

The piston and cylinder are of conventional design and may be formed from suitable metal or plastics material.

Figure 4:
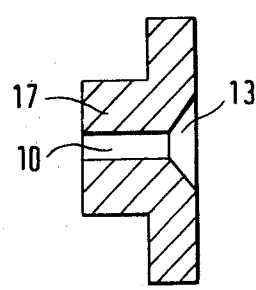
FIG. 4 is a sectional side-elevation of a modified replaceable disc.

The second embodiment is operated in a similar manner, except that in this case after screwing on the end-cap 6, the first replaceable disc 15 is inserted into the bore 5 before the liner 11. It will be apparent however that the second embodiment must be operated in a generally vertical sense, since otherwise material which has been extruded through the duct 13 will tend to fall against the side walls of the passage 16 and to adhere thereto. However, when operated in a generally vertical sense the second embodiment can be used with a metal cylinder for extrusion of those abrasive paste-like materials mentioned hereinbefore where contamination with metal must be avoided. Such pastes may also be extruded using the first embodiment but in this case it is necessary to use a non-metallic, for example nylon, end-cap 6. Alternatively, when it is desired to extrude such pastes in a generally horizontal sense, the first or second embodiments may be modified to provide a third embodiment in which the first replaceable disc (14 or 15) is adapted as illustrated in FIG. 4 by providing it with a central tubular extension 17 of the same internal diameter as the narrower part of the funnel-shaped duct 13, which extension fits within and is at least as long as the passage 16 in the end-cap 6.

When a batch of abrasive paste-like material has been extruded the piston 7 is withdrawn by the operating means from inside the space defined by the liner 11. The end-cap 6 is unscrewed from the body 4 and the replaceable discs are removed as a unit held together by a thin sandwich of abrasive paste-like material. The discs may then, depending on the extent of wear, either be discarded and replaced by a new pair, or cleaned and reinserted into the apparatus for extrusion of a further batch of material. Similarly, the liner 11 may either be discarded, or reused for a further batch of material without any significant cleaning being necessary.

The cutting means and piston operating means may be linked by conventional techniques in such a way that predetermined lengths of extruded material may be automatically cut off, thus enabling the apparatus to be used in conjunction with conventional automated filling lines.

It will be appreciated that although the extrusion apparatus of the invention has been described as comprising the known types of cylindrical piston operating in a generally complementary bore, they may also comprise a cylindrical piston having a significantly smaller diameter than that of the bore.

It will also be appreciated that the lining system can be used for temporary storage of a batch of abrasive paste prior to its extrusion when the liner is formed from continuous tube and the first and second disc are of the same diameter such that they are both a close but slidable fit within the space enclosed by the liner.

What is claimed is:

1. An extrusion apparatus including a piston and cylinder; said cylinder having a bore generally complementary to said piston and leading at its inner end to an external orifice, said bore having a side-wall, and operating means associated with said piston for causing paste-like material to be compressed within said bore and extruded through said external orifice; wherein the improvement consists essentially of a lining system for said cylinder comprising a tubular liner, a first replaceable disc, and a second replaceable disc, said liner and first and second discs each composed of plastics material selected from the group consisting essentially of polypropylene, polytetrafluoroethylene, high density polyethylene, and nylon;

said tubular liner formed as a thin sheet and having appropriate dimensions and resilience so as to assume an essentially tubular form without overlap when inserted into said bore, closely fitting against and substantially covering said side-wall of said bore;

said first replaceable disc substantially closing the end of said liner nearest said external orifice and defining a central hole having a diameter not larger than the diameter of said orifice; and said second replaceable disc substantially closing the other end of said liner, and shaped so that it is capable of slidable movement within the space enclosed by said liner under the influence of said piston and said operating means, so that said extrusion apparatus is useful for extruding dental filling compositions or like abrasive paste-like materials.

2. An improved extrusion apparatus according to claim 1 wherein both said first and second replaceable discs are of the same diameter such that they are both a close but slidable fit within the space enclosed by said liner.

3. An improved extrusion apparatus according to claim 1 wherein said liner has a wall thickness in the range 0.5-3.00 mm. and said replaceable discs are of thickness in the range 4.0-30.00 mm.

4. An improved extrusion apparatus according to claim 1 wherein a central tubular extension surrounds said hole defined in said first replaceable disc, said extension fitting in the length of said external orifice.

5. A method of extruding an abrasive paste-like dental filling composition utilizing an extrusion apparatus comprising a piston and cylinder, the cylinder having a bore generally complementary to the piston and leading at its inner end to an external orifice, and an operating device for the piston; said method comprising the steps of (a) preventing frictional wear occuring to the piston and the bore during utilization thereof by (i) cutting a rectangular thin sheet composed of a material consisting essentially of polypropylene, polytetrafluoroethylene, high density polyethylene, and nylon, to size to form a sheet liner, and inserting into the bore the thin sheet liner so that it assumes a tubular form without overlap, closely fitting against and substantially covering the side-wall of the bore; (ii) inserting into the bore a first replaceable disc having a central opening and composed of a material consisting essentially of polypropylene, polytetrafluoroethylene, high density polyethylene, and nylon, so that the first disc closes the end of the liner nearest the external orifice with the central opening therein in-line with the orifice, and having a diameter no larger than the diameter of the orifice; and (iii) inserting into the bore a second replaceable disc composed of a material consisting essentially of polypropylene, polytetrafluoroethylene, high density polyethylene, and nylon, so that the second disc is capable of slidable movement within the space enclosed by the liner;

(b) moving the piston with the operating device to extrude the filling composition from between the first and second discs and liner through the orifice; and (c) replacing the tubular liner and first and second discs when they become worn.

* * * * *